United States Patent
Heffels et al.

(10) Patent No.: US 10,871,443 B2
(45) Date of Patent: Dec. 22, 2020

(54) GAS ANALYZER FOR MEASURING NITROGEN OXIDES AND LEAST ONE FURTHER COMPONENT OF AN EXHAUST GAS

(71) Applicant: SIEMENS AKTIENGESELLSCHAFT, Munich (DE)

(72) Inventors: Camiel Heffels, Stutensee-Buechig (DE); Benjamin Schmidt, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 16/637,413

(22) PCT Filed: Jul. 16, 2018

(86) PCT No.: PCT/EP2018/069201
§ 371 (c)(1),
(2) Date: Feb. 7, 2020

(87) PCT Pub. No.: WO2019/029949
PCT Pub. Date: Feb. 14, 2019

(65) Prior Publication Data
US 2020/0200674 A1 Jun. 25, 2020

(30) Foreign Application Priority Data
Aug. 10, 2017 (DE) .................. 10 2017 213 980

(51) Int. Cl.
*G01N 21/33* (2006.01)
*G01N 21/85* (2006.01)
*G01N 33/00* (2006.01)

(52) U.S. Cl.
CPC ............ *G01N 21/33* (2013.01); *G01N 21/85* (2013.01); *G01N 33/0037* (2013.01);
(Continued)

(58) Field of Classification Search
CPC .... G01N 21/33; G01N 21/85; G01N 33/0037; G01N 33/0039; G01N 33/0042;
(Continued)

(56) References Cited

U.S. PATENT DOCUMENTS 5,806,305 A 9/1998 Miller et al.
7,846,739 B2 * 12/2010 von Bahr ............... G01N 27/28
436/116
(Continued)

FOREIGN PATENT DOCUMENTS

EP 1020620 7/2000
EP 2157421 2/2010
(Continued)

OTHER PUBLICATIONS

Higashi Ryoichi et al:"A NO and SO gas analyzer using deep-UV and violet light-emitting diodes for continuous emissions monitoring systems", Visual Communications and Image Processing, Bd. 9003, pp. 90031F-1-90031F-6, Figure 6; 2014.
(Continued)

*Primary Examiner* — Roy M Punnoose
(74) *Attorney, Agent, or Firm* — Cozen O'Connor

(57) ABSTRACT

A gas analyzer includes an oxidation device and a subsequent photometer, wherein the oxidation device has a reaction chamber located in an exhaust gas path and a heating chamber downstream thereof, where an ultraviolet light source generates ozone from residual oxygen content of the exhaust gas within the reaction chamber to convert nitrogen monoxide into nitrogen dioxide in the exhaust gas, nitrogen oxides and excess ozone are broken down into nitrogen
(Continued)

dioxide and oxygen in the heating chamber, the photometer outputs the measured nitrogen dioxide concentration as nitrogen oxide concentration of the untreated exhaust gas, and where an additional photometer is located in the exhaust gas path between the reaction chamber and the heating chamber which, via light absorption, measures the ozone concentration in the partially treated exhaust gas and outputs the same as oxygen concentration of the untreated exhaust gas.

12 Claims, 3 Drawing Sheets

(52) U.S. Cl.
CPC ..... *G01N 33/0039* (2013.01); *G01N 33/0042* (2013.01); *G01N 2021/8578* (2013.01); *G01N 2201/0625* (2013.01); *G01N 2201/121* (2013.01)

(58) Field of Classification Search
CPC ... G01N 2021/8578; G01N 2201/0625; G01N 2201/121

USPC .......................................................... 356/437
See application file for complete search history.

(56) References Cited

U.S. PATENT DOCUMENTS

| | | | |
|---|---|---|---|
| 2010/0049017 | A1 | 2/2010 | LeBoeuf et al. |
| 2011/0177607 | A1 | 7/2011 | Akasaka et al. |
| 2019/0317067 | A1* | 10/2019 | Heffels ............... G01N 31/005 |

FOREIGN PATENT DOCUMENTS

| | | | |
|---|---|---|---|
| JP | 07225214 | 8/1995 | |
| JP | 2004138467 | 5/2004 | |
| WO | WO2015181879 A1 * | 12/2015 | ............. G01N 21/33 |

OTHER PUBLICATIONS

PCT International Search Report dated Nov. 20, 2018 based on PCT/EP2018/069201.

* cited by examiner

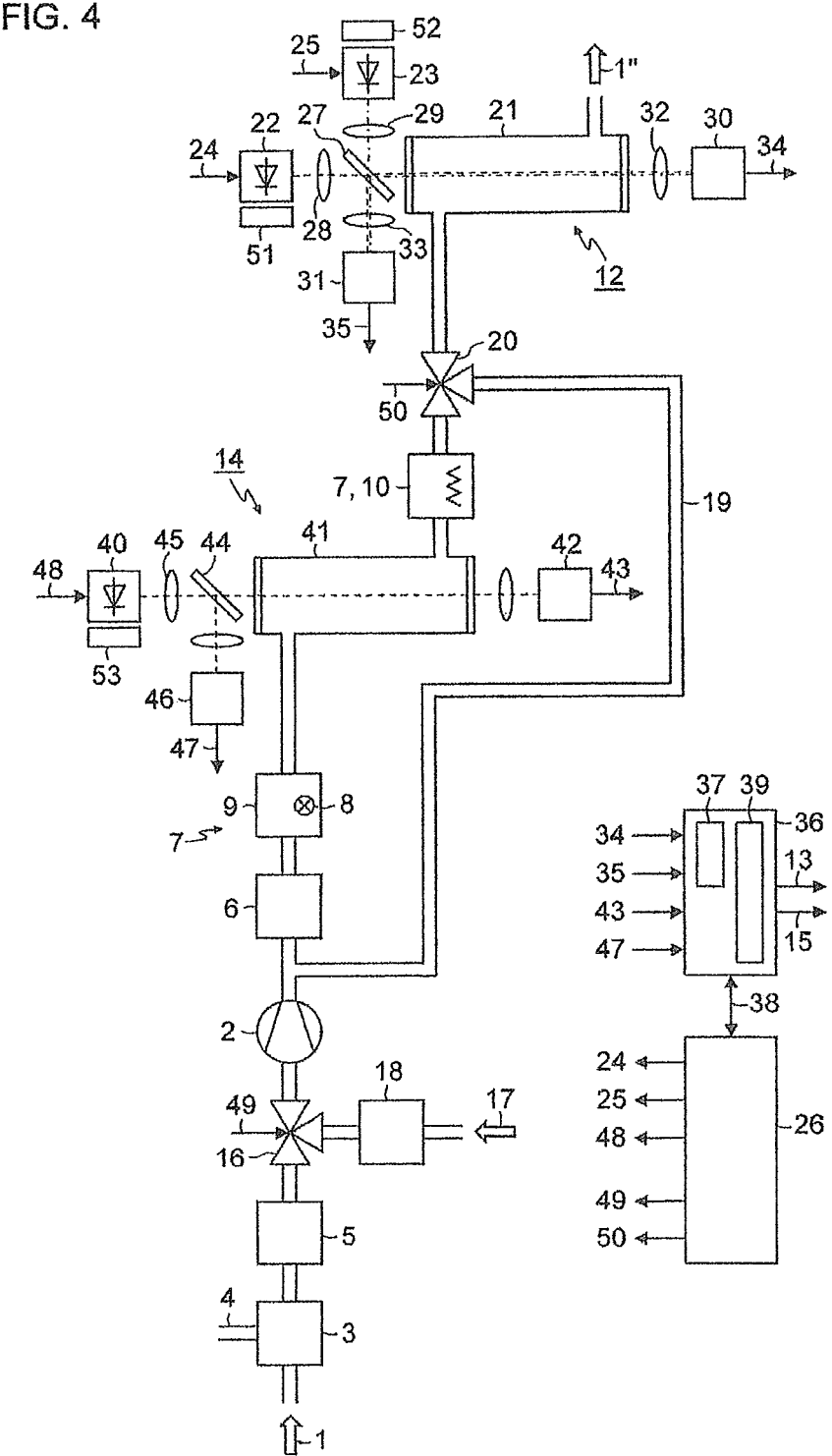

GAS ANALYZER FOR MEASURING NITROGEN OXIDES AND LEAST ONE FURTHER COMPONENT OF AN EXHAUST GAS

CROSS-REFERENCE TO RELATED APPLICATIONS

This is a U.S. national stage of application No. PCT/EP2018/069201 filed Jul. 16, 2018. Priority is claimed on German Application No. 102017213980 filed Aug. 10, 2017, the content of which is incorporated herein by reference in its entirety.

BACKGROUND OF THE INVENTION

1. Field of the Invention

The invention relates to a gas analyzer for measuring nitrogen oxides and at least one further component of an exhaust gas with an oxidation device comprising an ozone generator, a reaction chamber located in an exhaust gas path and a heating chamber located downstream thereof in the exhaust gas path and which is configured to treat the exhaust gas with generated ozone in the reaction chamber to convert nitrogen monoxide into nitrogen dioxide and to induce thermal decomposition of nitrogen oxides and excess ozone into nitrogen dioxide and oxygen in the heating chamber and with a photometer located downstream of the oxidation device in the exhaust gas path, which is configured to ascertain the nitrogen dioxide concentration based on the absorption of light in the near-ultraviolet range between 350 nm and 500 nm the treated exhaust gas and output the same as the nitrogen oxide concentration of the untreated exhaust gas.

2. Description of the Related Art

A gas analyzer with a photometer for measuring nitrogen oxides and sulfur dioxide in an exhaust gas is disclosed in Ryoichi Higashi et al.: "A NOx and SO2 gas analyzer sing deep-UV and violet light-emitting diodes for continuous emissions monitoring Systems", Proc. SPIE 9003, Light-Emitting Diodes: Materials, Devices, and Applications for Solid State Lighting XVIII, 90031F (Feb. 27, 2014). Before analysis, the exhaust gas is treated in two stages, where within a first stage nitrogen monoxide contained in the exhaust gas is converted with the aid of ozone into nitrogen dioxide that can be measured by the photometer. The ozone is generated from atmospheric oxygen by electric discharge and fed to the exhaust gas. In a second treatment stage, the exhaust gas is heated to approximately 300° C. to induce thermal decomposition of excess ozone and dinitrogen pentoxide ($N_2O_5$) formed by the reaction of nitrogen dioxide and ozone and which cannot be measured with the photometer into nitrogen dioxide. Hence, the concentration of nitrogen dioxide ascertained by the gas analyzer is a measure for the concentration of nitrogen oxides in the exhaust gas.

In the photometer of the conventional gas analyzer, a first light-emitting diode with an emission wavelength of 280 nm and a second light-emitting diode with an emission wavelength of 400 nm are arranged closed to one another in an LED array. A collimator lens shapes their light into a parallel light bundle, which passes through a measuring chamber through which the treated exhaust gas flows and is then focused on a detector. A beam splitter between the collimator lens and the measuring chamber diverts a part of the light to a monitor detector. The light-emitting diodes are switched on and off alternately to detect the sulfur dioxide contained in the exhaust gas at the absorption wavelength of 280 nm and nitrogen dioxide at the absorption wavelength of 400 nm. The detector signal is normalized with the signal of the monitor detector before being evaluated to ascertain the sulfur dioxide and nitrogen dioxide or nitrogen oxide concentrations in the exhaust gas. The temperature of the light-emitting diodes is regulated to a constant value by means of a Peltier element.

U.S. Pat. No. 5,806,305 A discloses a device for catalytic treatment of exhaust gases of internal combustion engines (gasoline or diesel engines) with which ozone is supplied to the exhaust gas before treatment in the catalyst. The ozone is generated in an ozone generator from fresh air via UV light, for example, a mercury vapor lamp at a wavelength of 185 nm.

EP 1 020 620 E1 discloses, with respect to the same object, the generation of ozone from fresh air or the exhaust gas by means of UV light, microwave energy or spark discharge.

It is known from EP 2 157 421 A1 to assay the sulfur content of fuel by combusting a sample of the fuel and determining the concentration of sulfur dioxide in the exhaust gas by an ultraviolet fluorescence method. In order to avoid interference from nitrogen monoxide in the assays, the exhaust gas is first exposed in a container to the light (185 nm) from a low-pressure mercury discharge lamp to generate ozone from the residual oxygen content and thus convert nitrogen monoxide into nitrogen dioxide.

SUMMARY OF THE INVENTION

It is an object of the invention to enable a determination of the oxygen concentration in exhaust gases together with the measurement of nitrogen oxides.

This and other objects and advantages are achieved in accordance with the invention by a gas analyzer in which the ozone generator includes an ultraviolet light source arranged in the reaction chamber, which generates the ozone from the residual oxygen content of the exhaust gas, and arranged in the exhaust gas path between the reaction chamber and the heating chamber, there is a further photometer, which is configured to ascertain the ozone concentration in the partially treated exhaust gas based on the absorption of light in the mid-ultraviolet range between 220 nm and 300 nm and to output the same as the oxygen concentration of the untreated exhaust gas.

The disadvantage of the generation of ozone from atmospheric oxygen as mentioned in the publication by Ryoichi Higashi et al via electric discharge (corona discharge), is the formation of nitrogen oxide compounds that are undesirable for the measurement of nitrogen oxide in the exhaust gas. Therefore, the oxidation device of the gas analyzer in accordance with the invention preferably comprises an ozone generator with an ultraviolet light source that generates high-energy radiation with a wavelength of less than 240 nm, such as an electrodeless excimer lamp or a low-pressure mercury discharge lamp, in the reaction chamber through which the exhaust gas flows. Lean combustion with excess air enables the ozone to be generated completely from the residual oxygen content of the exhaust gas. The reaction chamber can, for example, take the form of a tube with an internal mirror coating (for example an aluminum tube in which the, for example, cylindrical ultraviolet light source extends. To enhance performance during the conversion of nitrogen monoxide into nitrogen dioxide, a plurality of such tubes can be connected in parallel. If the performance of the ultraviolet light source deteriorates over time, then the exhaust gas can be additionally supplied with atmospheric oxygen.

In the reaction chamber, the conversion of oxygen to ozone occurs in proportion to the oxygen concentration and ultraviolet light output present in the exhaust gas. The concentration of the nitrogen monoxide typically lies in the range of up to 100 ppm, while the residual oxygen content of the exhaust gas stays in the range of a few vol %, i.e. at >10,000 ppm. Consequently, only comparatively small amount of ozone is consumed in the conversion of nitrogen monoxide into nitrogen dioxide. Therefore, with a constant throughflow of the exhaust gas (and hence a constant residence time in the reaction chamber), the ozone concentration in the partially treated exhaust gas on leaving the reaction chamber is a measure for the oxygen concentration in the untreated exhaust gas. The further photometer measures the ozone concentration based on the light absorption in the mid-ultraviolet range between 220 nm and 300 nm and outputs this as the oxygen concentration of the untreated exhaust gas. The proportionality factor of the virtually linear relationship between the oxygen concentration and the ozone concentration can be ascertained very easily by calibration.

The cross-sensitivity between the sulfur dioxide concentration and the measured value generated by the further photometer for the ozone or oxygen concentration is compensated by computational measures. The cross-sensitivity between the nitrogen dioxide concentration and the measured value generated by the photometer for the sulfur dioxide concentration is also compensated by computational measures.

If the exhaust gas is guided past the oxidation device to the photometer with the aid of a bypass, then the nitrogen dioxide concentration of the untreated exhaust gas is obtained. The difference between the nitrogen dioxide concentrations measured in the treated exhaust gas and the untreated exhaust gas produces the nitrogen monoxide concentration of the untreated exhaust gas, which is also a measure for ozone consumption in the oxidation device on the conversion of nitrogen monoxide into nitrogen dioxide. Therefore, the result for the oxygen concentration of the untreated exhaust gas is corrected by the amount of the ascertained nitrogen monoxide concentration.

The ultraviolet output of the illuminant in the ozone generator deteriorates over time. As a result, it may be necessary to supply the gas analyzer with atmospheric air with vol % oxygen on a regular basis. This resets the end value of the ozone measurement and the zero point of the sulfur dioxide and nitrogen dioxide measurements of the two photometers once again.

If, as in the start-up and combustion shutdown internal engine, there is a high nitrogen dioxide concentration in the exhaust gas, instead of the three-way valve, then it is also possible for a third photometer connected parallel to the two photometers to be provided to measure the nitrogen dioxide concentration in the exhaust gas.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be explained with reference to examples for which purpose reference is made to the figures in the drawing, in which:

FIG. 4 is a more detailed schematic block diagram illustrating an exemplary embodiment of the gas analyzer in accordance with the invention.

DETAILED DESCRIPTION OF THE EXEMPLARY EMBODIMENTS

Figure 1:
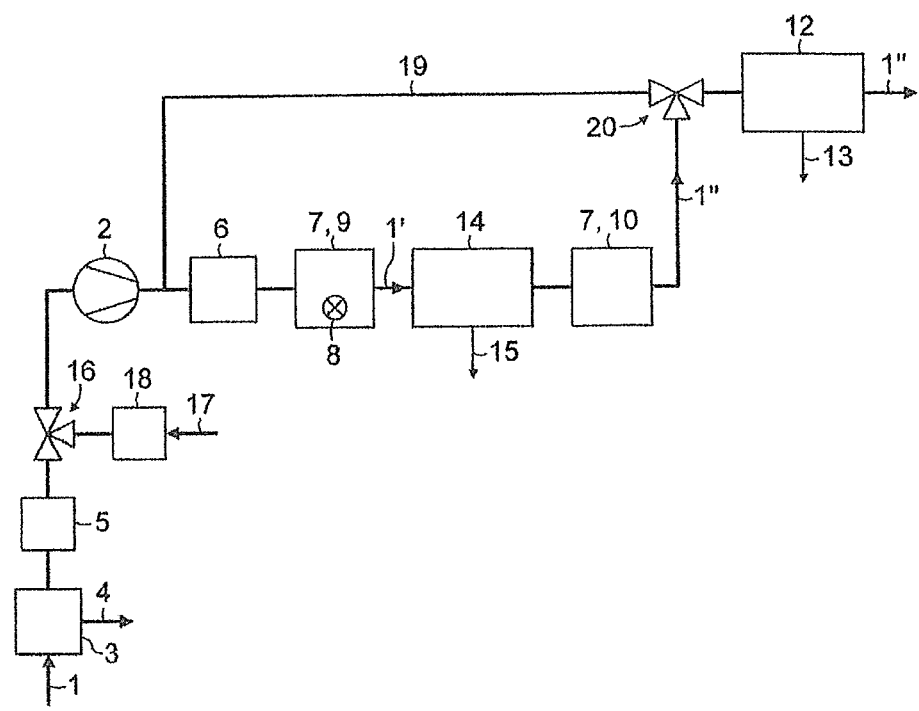
FIG. 1 is a block diagram illustrating the gas analyzer the for measuring nitrogen oxides, sulfur dioxide and oxygen in accordance with the invention.

FIG. 1 shows a simplified schematic representation of a block diagram of a gas analyzer for measuring nitrogen oxides, sulfur dioxide and oxygen in an exhaust gas 1. The exhaust gas 1 is drawn in via a sample gas pump 2 from a sampling point through a gas cooler 3 with a condensate outlet 4 and a fine particle filter 5. The gas cooler 3 serves to prevent condensation of water in the gas analyzer. The throughflow of the exhaust gas 1 is set as constant with the aid of a throughflow regulator 6 in the form of a mass throughflow regulator or pressure regulator with a subsequent throttle.

In order to facilitate the measurement of the nitrogen oxide concentration, the exhaust gas 1 is treated in a two-stage oxidation device 7, which comprises an ozone generator in the form of an ultraviolet light source 8 in a reaction chamber 9 through which the exhaust gas 1 flows in a first stage and a heating chamber 10 in a second stage. With its radiation of, for example, 185 nm, the ultraviolet light source 8, which is, for example, an electrodeless excimer lamp or a low-pressure mercury discharge lamp, generates ozone from the residual oxygen of the exhaust gas 1, which converts nitrogen monoxide contained in the exhaust gas 1 into nitrogen dioxide in the reaction chamber 9. The amount of ozone generated is proportional to the oxygen content of the exhaust gas 1 and the UV output of the light source 8. A constant throughflow of the exhaust gas 1 is important because the ozone production is also dependent upon the residence time of the oxygen in the ozone generator and decreases if the mass flow is too high. However, the existing or converted nitrogen dioxide can react again with the ozone generated, where further nitrogen oxides, particularly dinitrogen pentoxide, are formed. In the heating chamber (gas heater) 10, these undesirable nitrogen oxides and excess ozone are thermally decomposed at about 300° C. to form nitrogen dioxide and oxygen.

Figure 2:
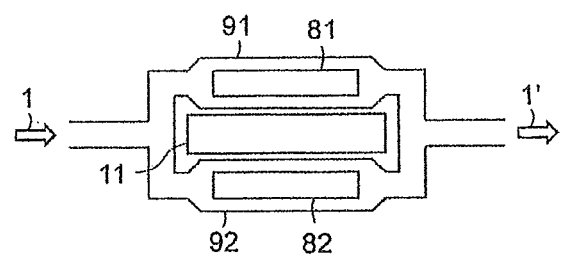
FIG. 2 is a schematic block diagram illustrating an exemplary embodiment of the ozone generator in accordance with the invention.

FIG. 2 is a very simplified depiction of an exemplary embodiment of the ozone generator, here with two ultraviolet light sources 81, 82 in the form of cylindrical low-pressure mercury discharge lamps that are arranged in two aluminum tubes 91, 92 with an internal mirror coating that are connected in parallel and through which the exhaust gas 1 flows. The tubes 71, 72 form the reaction chamber 9. The mercury plasma can be excited via electrodes or, to extend the service life, in an electrodeless manner by means of a microwave generator 11.

Returning to FIG. 1, after leaving the heating chamber 10, the treated exhaust gas 1" is fed to a photometer 12, which measures the concentrations of nitrogen dioxide and sulfur dioxide based on the absorption of light each case range of the wavelengths of 405 nm and 285 nm. The nitrogen dioxide concentration of the treated exhaust gas 1" is the sum of the nitrogen dioxide concentration and the concentration of the nitrogen monoxide of the untreated exhaust gas 1 that has been converted to nitrogen dioxide, in addition to the sulfur dioxide concentration. As a result, the photometer 12 outputs the nitrogen oxide concentration of the exhaust gas 1 to be analyzed as the analysis result 13.

Arranged in the exhaust gas path between the reaction chamber 9 of the oxidation device 7 and the heating chamber 10 there is a further photometer 14, which measures the concentrations of ozone in the partially treated exhaust gas 1' coming from the reaction chamber 9 based on the absorption of light in the wavelength range of 285 nm. As already mentioned, the amount of ozone generated by the ultraviolet light source 8 in the reaction chamber 9 is proportional to the oxygen content of the exhaust gas 1. Consequently, the further photometer 14 outputs the oxygen concentration of the exhaust gas 1 to be analyzed as the analysis result 15.

As explained below, based on FIG. 4, the two photometers 12, 14 are LED photometers with light-emitting diodes.

Figure 3:
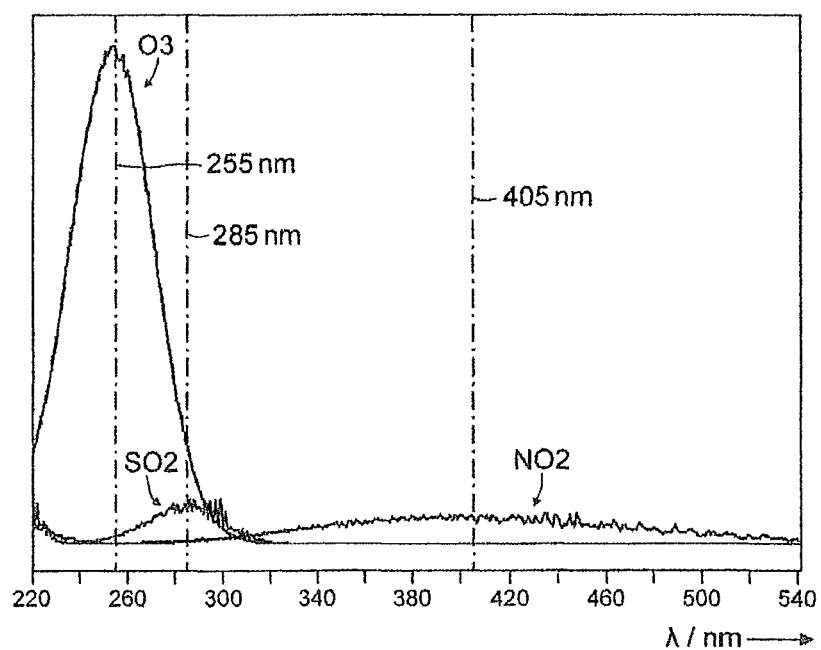
FIG. 3 in an exemplary graphical plot of the absorption spectra of nitrogen dioxide, sulfur dioxide and ozone and the central wavelengths of the emission spectra of the light-emitting diodes for measuring these components.

FIG. 3 shows an exemplary graphical plot of the absorption spectra of nitrogen dioxide NO2, ozone O3 and sulfur dioxide SO2 and the emission spectra of the light-emitting diodes represented here by the central wavelengths of 405 nm, 255 nm and 285 nm for measuring said components.

Returning to FIG. 1, arranged in the exhaust gas path before the oxidation device 7, there is a controllable three-way mixing valve 16 to enable atmospheric oxygen 17 to be mixed with the exhaust gas 1 when required by drawing it in via the sample gas pump 2 though a fine particle filter 18. The mixing can be performed manually or automatically, controlled by the further photometer 14, if the residual oxygen content of the exhaust gas 1 or the performance of the ozone generator 8 is not sufficient for the ozone generation required for the complete conversion of nitrogen monoxide into nitrogen dioxide.

A bypass 19, which can be switched on via a controllable three-way valve 20 to bypass the oxidation device 7, is provided between the sample gas pump 2 and the photometer 12. When the bypass 19 is switched on, the untreated exhaust gas 1 enters the photometer 12 so that this measures the nitrogen dioxide concentration of the exhaust gas 1 instead of the nitrogen oxide concentration. The nitrogen dioxide concentration in the exhaust gas 1 is generally low in the case of a stationary combustion process. As a result, the bypass 19 is normally switched off and so the nitrogen oxide concentration is measured. However, if the residual oxygen content of the exhaust gas 1 is low, then the nitrogen monoxide concentration in the exhaust gas 1 may be required in order to take account of the ozone loss in the reaction chamber 9 due to the oxidation of the nitrogen monoxide during the ozone generation in the calculation of the oxygen concentration. The nitrogen monoxide concentration is then obtained from the difference between the nitrogen dioxide concentrations measured in the treated exhaust gas 1" and the untreated exhaust gas 1. This difference corresponds to the proportion of the nitrogen dioxide contained in the treated exhaust gas 1", which results from the conversion of nitrogen monoxide with ozone, and is therefore not measured by the further photometer 14, and is therefore a measure for the ozone loss to therefore correct the result 15 output by the further photometer 14 for the oxygen concentration by the amount of the ascertained nitrogen monoxide concentration.

If, as in the case of the start-up and shutdown of the internal combustion machine, there is a high nitrogen dioxide concentration in the exhaust gas 1, instead of the three-way valve 20, then it is also possible for a third photometer connected in parallel to the two photometers 12, 14 to be provided to measure the nitrogen dioxide concentration in the exhaust gas 1.

FIG. 4 shows a more detailed exemplary embodiment of the gas analyzer in accordance with the invention. As already shown in FIG. 1, the exhaust gas 1 is drawn in by the sample gas pump 2 from via the gas cooler 3 with the condensate outlet 4 and the fine particle filter 5, where the throughflow thereof is set as constant with the aid of the throughflow regulator 6. The exhaust gas 1 is treated in the oxidation device 7, where it first passes through reaction chamber 9 with the ultraviolet light source 8 and the heating chamber 10. The downstream photometer 12 measures the nitrogen dioxide and sulfur dioxide concentrations in the treated exhaust gas 1". The further photometer 14 measures the concentrations of ozone of the partially treated exhaust gas 1' in the exhaust gas path between the reaction chamber 9 and the heating chamber 10. The three-way mixing valve 16 arranged in the exhaust gas path before the oxidation device 7 facilitates the admixture of atmospheric oxygen 17 that is drawn in by the sample gas pump 2 through the fine particle filter 18. The bypass 19 that can be switched on via the three-way valve 20 enables the untreated exhaust gas 1 to be directed into the photometer 12 by bypassing the oxidation device 7.

The photometer 12 comprises a measuring chamber 21 through which the treated exhaust gas 1" is guided and through which the light from a first light-emitting diode 22 with the central wavelength of 405 nm and a second light-emitting diode 23 with the central wavelength of 285 nm passes. The two light-emitting diodes 22, 23 are actuated differently with control signals 24, 25 from a control device 26, for example, switched on and off alternately or modulated differently, for example, with different modulation frequencies, clock rates or pulse codes. The two light-emitting diodes 22, 23 can, for example, be arranged closed to one another in an LED array. In the example shown, the light-emitting diodes 22, 23 are arranged opposite different sides of a beam splitter 27, which splits the light from the light-emitting diodes 22, 23 collimated by lenses 26, 29 into a partial beam through the measuring chamber 21 to a detector 30 and a further partial beam to a reference detector 31. The two partial beams can be focused with the aid of lenses 32, 33 onto the detectors 22, 23, which in this case are photodiodes.

The detector 3G generates a detector signal 34 with a first signal component resulting from the light from the first light-emitting diode 22 and a second signal component resulting from the light from the second light-emitting diode 23. The reference detector 31 generates a reference signal 35 with reference signal components resulting from the light from both light-emitting diodes 22, 23. The detector signal 34 and the reference signal 35 are supplied to an evaluation device 36 containing a demultiplexer or demodulator 37 to separate the different signal components of the detector signal 34 and the reference signal 35 for the further processing and evaluation. The different actuation of the light-emitting diodes 22, 23 and the detection of the different signal components are synchronized via a communication line 38 between the control device 26 and the evaluation device 36. After conditioning, such as filtering and digitizing, of the signals 34, 35, a computing device 39 ascertains the nitrogen dioxide concentration of the treated exhaust gas 1" from the first signal component of the detector signal 34 and the sulfur dioxide concentration from the second signal component. Herein, the signal components of the detector signal 34 are referenced with the associated signal components of the reference signal 35 so that the analysis result 13 output is independent of the brightness of the light-emitting diodes 22, 23 and hence, for example, of their state of ageing. In the analysis result 13, the nitrogen dioxide concentration of the treated exhaust gas 1" is output as the nitrogen oxide concentration of the untreated exhaust gas 1.

In the further photometer 14, the light with the central wavelength of 255 nm from a third light-emitting diode 40 is guided through a further measuring chamber 41 to a further detector 42, which generates a further detector signal 43. Here, once again, a beam splitter 44 splits the light collimated by a lens 45 into a partial beam through the further measuring chamber 41 and a further partial beam onto a further reference detector 46. The evaluation device 36 ascertains the ozone concentration of the partially treated exhaust gas 1' from the further detector signal 43 and the reference signal 47 from the further reference detector 46 in order to output this in the analysis result 15 as the oxygen concentration of the untreated exhaust gas 1. The third light-emitting diode 40 can also be actuated by a control signal 48 from the control device 26 in order, for example, to modulate the generated light and thus render the measurement insensitive to the influences of extraneous light. The control device 26 also generates control signals 49, 50 for the valves 16, 20.

Despite the aforementioned referencing of the measurements, thermostatic regulation of the entire photometric measuring arrangement of the gas analyzer is advantageous. This also includes thermostatic regulation of the light-emitting diodes 22, 23, 40 with the aid of Peltier elements 51, 52, 53 in order to be able to achieve measuring ranges in the lower ppm range.

Instead of the common evaluation device 36 shown, each of the two photometers 12, 14 can have its own evaluation device, where these communicate with one another.

The gas analyzer shown can readily be expanded for the measurement of further constituents of the exhaust gas 1, such as carbon dioxide, carbon monoxide, sulfur compounds, chlorine compounds and iodine compounds. Instead of the further suitable light sources required to this end (for example, light-emitting diodes and possibly further beam spiltters in the photometer 12, it is possible for individual existing light-emitting diodes to be provided with a luminescent material (phosphor) that partially converts the light generated by the relevant light-emitting diode into light with a larger wavelength. This principle is, for example, Known from US 2010/049017 A1.

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas analyzer for measuring nitrogen oxides and at least one further component of an exhaust gas, the gas analyzer comprising:
   an oxidation device including an ozone generator, a reaction chamber located in an exhaust gas path, and a heating chamber located downstream thereof in the exhaust gas path, the oxidation device being configured to treat the exhaust gas with generated ozone in the reaction chamber to convert nitrogen monoxide into nitrogen dioxide and to induce thermal decomposition of nitrogen oxides and excess ozone into nitrogen dioxide and oxygen in the heating chamber;
   a photometer located downstream of the oxidation device in the exhaust gas path, the photometer being configured to ascertain a concentration of the nitrogen dioxide based on absorption of light in a near-ultraviolet range between 350 nm and 500 nm in the treated exhaust gas and output said concentration as a nitrogen oxide concentration of the untreated exhaust gas; and
   a further photometer arranged in the exhaust gas path between the reaction chamber and the heating chamber, said further photometer being configured to ascertain an ozone concentration in partially treated exhaust gas based on absorption of light in a mid-ultraviolet ultraviolet range between 220 nm and 300 nm and to output the said concentration as an oxygen concentration of the untreated exhaust gas;
   wherein the ozone generator includes an ultraviolet light source arranged in the reaction chamber which generates ozone from a residual oxygen content of the exhaust gas.

2. The gas analyzer as claimed in claim 1, wherein the photometer and the further photometer each comprise a measuring chamber through which the exhaust gas flows, a light-emitting diode generating the light, a detector, a reference detector, an evaluation device and a beam splitter, which is configured to guide a part of the light from the light-emitting diodes through the measuring chamber to the detector and another part of the light to the reference detector; and
   wherein the evaluation device references the detector signal with the reference signal.

3. The gas analyzer as claimed in claim 2, wherein the photometer is further configured to ascertain sulfur dioxide concentration of the exhaust gas based on the absorption of light in the mid-ultraviolet range between 250 nm and 300 nm in the exhaust gas and output the sulfur dioxide concentration.

4. The gas analyzer as claimed in claim 2, wherein the photometer comprises a second light-emitting diode generating the light in the mid-ultraviolet range between 350 nm and 500 nm;
   wherein the beam splitter is configured to guide a part of the light from the second light emitting diode through the measuring chamber to the detector and the other part of the light to the reference detector;
   wherein a control device is present which actuates the first light-emitting diode and the second light-emitting diode differently such that a detector signal and a reference signal each contain different signal components each resulting from the light from the first light-emitting diode and the light from the second light emitting diode; and wherein the evaluation device ascertains the nitrogen dioxide concentration of the exhaust gas from a signal component of the detector signal resulting from the light from the first light-emitting diode and the sulfur dioxide concentration from the signal component resulting from the light from the second light-emitting diode.

5. The gas analyzer as claimed in claim 4, wherein the photometer and further photometer each have two evaluation devices that communicate with one another or a common evaluation device that is configured to correct a cross sensitivity of the ascertained sulfur dioxide concentration of the exhaust gas to nitrogen dioxide with the ascertained nitrogen dioxide concentration of the exhaust gas.

6. The gas analyzer as claimed in claim 2, wherein the photometer and further photometer each have two evaluation devices that communicate with one another or a common evaluation device that is configured to correct a cross sensitivity of the ascertained sulfur dioxide concentration of the exhaust gas to nitrogen dioxide with the ascertained nitrogen dioxide concentration of the exhaust gas.

7. The gas analyzer as claimed in claim 6, wherein the evaluation device is configured to correct the cross sensitivity between the ascertained ozone concentration of the exhaust gas and sulfur dioxide with the ascertained sulfur dioxide concentration of the exhaust gas.

8. The gas analyzer as claimed in claim 1, wherein the photometer is further configured to ascertain sulfur dioxide concentration of the exhaust gas based on the absorption of light in the mid-ultraviolet range between 250 nm and 300 nm in the exhaust gas and output the sulfur dioxide concentration.

9. The gas analyzer as claimed in claim 8, wherein the photometer comprises a second light-emitting diode generating the light in the mid-ultraviolet range between 350 nm and 500 nm;

wherein the beam splitter is configured to guide a part of the light from the second light emitting diode through the measuring chamber to the detector and the other part of the light to the reference detector;

wherein a control device is present which actuates the first light-emitting diode and the second light-emitting diode differently such that a detector signal and a reference signal each contain different signal components each resulting from the light from the first light-emitting diode and the light from the second light emitting diode; and wherein the evaluation device ascertains the nitrogen dioxide concentration of the exhaust gas from a signal component of the detector signal resulting from the light from the first light-emitting diode and the sulfur dioxide concentration from the signal component resulting from the light from the second light-emitting diode.

10. The gas analyzer as claimed in claim 8, wherein the photometer and further photometer each have two evaluation devices that communicate with one another or a common evaluation device that is configured to correct a cross sensitivity of the ascertained sulfur dioxide concentration of the exhaust gas to nitrogen dioxide with the ascertained nitrogen dioxide concentration of the exhaust gas.

11. The gas analyzer as claimed in claim 1, further comprising:

a controllable bypass for bypassing the oxidation device which, when activated, the photometer measures the nitrogen dioxide concentration in the untreated exhaust gas and outputs the difference from the nitrogen dioxide concentration ascertained for the treated exhaust gas as the nitrogen monoxide concentration of the untreated exhaust gas.

12. The gas analyzer as claimed in claim 11, wherein the evaluation device is configured to correct a result of the ozone concentration of the oxygen concentration of the untreated exhaust gas supplied by the further photometer with the ascertained nitrogen monoxide concentration of the untreated exhaust gas.

* * * * *